US008575130B2

(12) United States Patent
Wu

(10) Patent No.: US 8,575,130 B2
(45) Date of Patent: Nov. 5, 2013

(54) MIXTURE OF HYALURONIC ACID FOR TREATING AND PREVENTING INFLAMMATORY BOWEL DISEASE

(75) Inventor: Tsung-Chung Wu, Taipei County (TW)

(73) Assignee: Holy Stone Healthcare Co., Ltd., Taipei (TW)

( * ) Notice: Subject to any disclaimer, the term of this patent is extended or adjusted under 35 U.S.C. 154(b) by 78 days.

(21) Appl. No.: 12/851,031

(22) Filed: Aug. 5, 2010

(65) Prior Publication Data

US 2011/0166100 A1    Jul. 7, 2011

Related U.S. Application Data

(63) Continuation-in-part of application No. 12/651,712, filed on Jan. 4, 2010.

(51) Int. Cl.
*A01N 43/04* (2006.01)
*A61K 31/715* (2006.01)

(52) U.S. Cl.
USPC .......................................................... 514/54

(58) Field of Classification Search
None
See application file for complete search history.

(56) References Cited

U.S. PATENT DOCUMENTS

| 5,888,986 A | 3/1999 | Morales et al. |
| 7,354,910 B2 | 4/2008 | Kono |
| 2005/0080037 A1 | 4/2005 | Petrella |

FOREIGN PATENT DOCUMENTS

| BE | 904547 | 10/1986 |
| HU | 203372 | 7/1991 |
| WO | WO87/05517 | 9/1987 |

OTHER PUBLICATIONS

Healia, "Irritable Bowel syndrome (IBS) Guide", Healia, http://www.healia.com/healthguide/guides/irritable-bowel-syndrome-ibs, Jan. 12, 2009.*
Worden, Irritable bowel syndrome (IBS), Netdoctor, http://www.netdoctor.co.uk/diseases/facts/irritablecolon.htm.*
WebMD, Ulcerative Colitis Prevention, WebMD, http://www.webmd.com/ibd-crohns-disease/ulcerative-colitis/ulcerative-colitis-prevention, Oct. 7, 2010.*
The New York Times, Enteritis Overview, The New York Times, http://health.nytimes.com/health/guides/disease/enteritis/overview.html?print=1, Jan. 2011.*
The University of Maryland Medical Center website, Crohn's disease, http://www.umm.edu/altmed/articles/crohns-disease-000043.htm, 2011.*
Gomis et al. Arthritis & Rheumatism vol. 50, No. 1, Jan. 2004, pp. 314-326.*
Definition of prevent, WordNet Search, downloaded from the internet Dec. 15, 2008.*
Worden, Irritable Bowel Syndrome (IBS), Netdoctor, http://www.netdoctor.co.uk/disease/facts/irritablecolon.htm, Dec. 14, 2010.*

* cited by examiner

*Primary Examiner* — Layla Bland
(74) *Attorney, Agent, or Firm* — Muncy, Geissler, Olds & Lowe, PLLC

(57) ABSTRACT

The present invention is related to a hyaluronic acid formulation including a mixture of hyaluronic acids having different weight-average molecular weight and different rheological, tissue scaffold, insulation and degradation properties in aqueous solution. The resulting formulation demonstrated an optimal balance between adhesion, tissue scaffold, insulation and treating time on the treatment and prevention of IBD (inflammatory bowel disease) such as ulcerative colitis and Crohn's disease. Thus, the formulation of the present invention exhibits a quick and lasting effect on the treatment and prevention of duodenal or peptic ulcer and bleeding which is very good thing indeed.

8 Claims, 1 Drawing Sheet

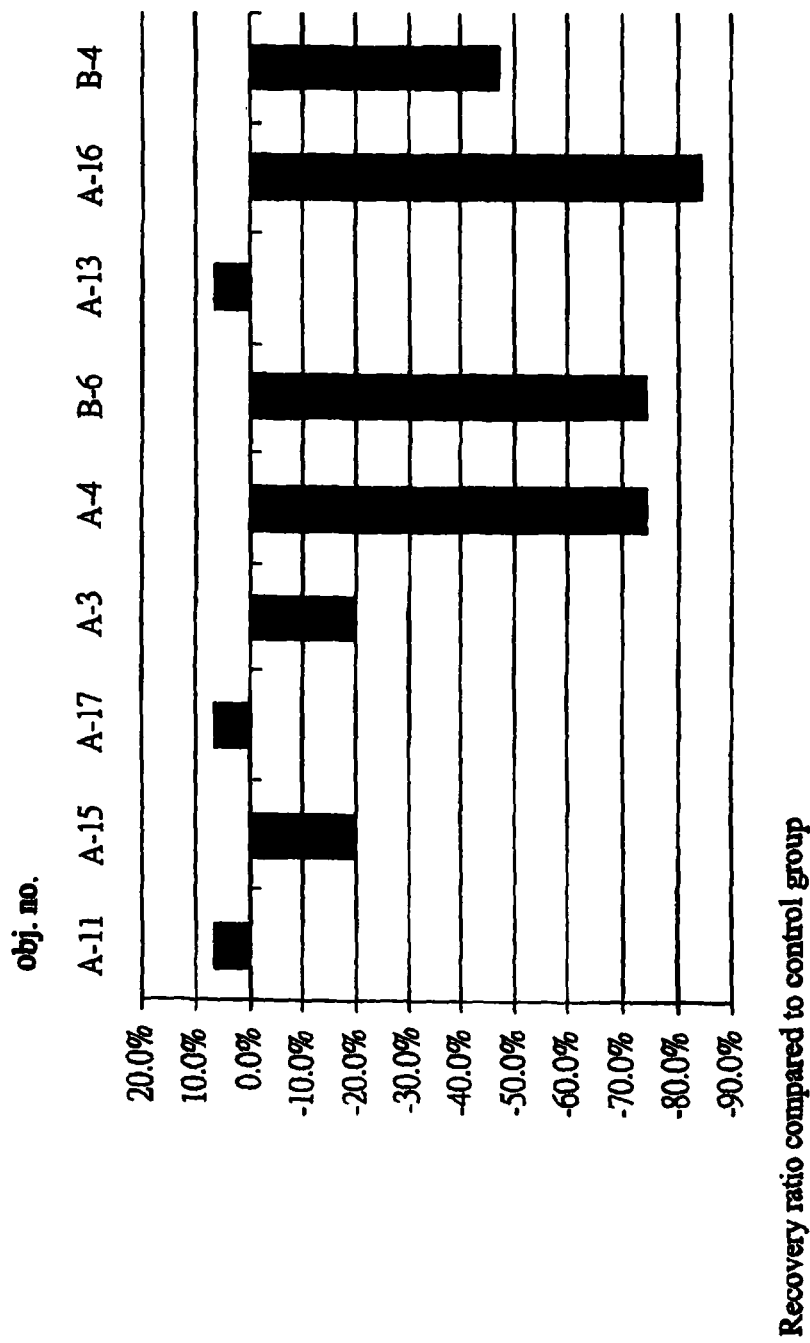

MIXTURE OF HYALURONIC ACID FOR TREATING AND PREVENTING INFLAMMATORY BOWEL DISEASE

This application is a Continuation-In-Part of application Ser. No. 12/651,712, filed on Jan. 4, 2010, now pending. The patent application identified above is incorporated here by reference in its entirety to provide continuity of disclosure.

BACKGROUND OF THE INVENTION

1. Field of the Invention

The present invention provides a mixture of the hyaluronic acid for treating and preventing the inflammatory bowel disease (IBD). More particularly, the present invention relates to a mixture comprising at least two or more than two different average hyaluronic acid molecular weights (Mw) and hyaluronic acid with different rheology to gain a hyaluronic acid with the proper adhesion property, functions of tissue scaffold and insulation and treatment time, in order to treat and to prevent IBD (inflammatory bowel disease) includes ulcerative colitis, Crohn's disease or wound healing in stomach and intestine, thus to achieve the prompt treatment and to prolong the effect.

2. Description of Related Art

Hyaluronic acid also known as hyaluronan, hyaluronate and sodium hyaluronate, and generally referred to as HA, which is a natural glycosaminoglycan including the alternative N-acetyl-D-glucosamine and D-glucuronic acid moiety.

The macromolecule of hyaluronic acid in sodium salt form generally is the known composition existing for over fifty years. Referring to Meyer and et al (J. Biol Chem. 107,629 (1934)), the hyaluronic acid intrinsically contains the high-viscosity glycosamine alternative with $\beta$ 1-3 glycuronic acid and $\beta$ 1-4 glycosamine, and the Mw of the high-viscosity glycosamine is between 50,000 Dalton (Da) and few million Dalton.

We can find the hyaluronic acid in the soft connective tissue in the body of mammals, and the skin, the vitreous humor of the eye, the synovial fluid, the umbilical cord and cartilage tissue contains higher volume of the hyaluronic acid.

The hyaluronic acid is the fluid with the elasticity, filling between the cells and the collagenous fibers and covering onto some epidermal tissues, majorly for the protection and the lubricant to cells for providing a platform for transporting the regulatory T cell to stabilize and to protect collagen network from the mechanical damage. The hyaluronic acid can be the lubricant in the tendon and the tendon sheath and on the surface of the synovial membrane due to the lubricant feature and the high shock absorber, and it is helpful for the tissue rheological mechanics, motion and the cell proliferation (referring to Delpech, B., Girard, N., Bertrand, P., Courel, M.-N., Chauzy, C., Delpech, A., 1997. Hyaluronan: fundamental principles and applications in cancer. J. Intern. Med. 242, 41-48, Rooney, P., Kumar, S., Ponting, J., Wang, M., 1995. The role of hyaluronan in tumour neovascularization. Int. J. Cancer 60, 632-36, Entwistle J, Hall C L, Turley EA Receptors: regulators of signaling to the cytoskeleton. J Cell Biochem 1996; 61: 569-77), and participating the receptor interaction on the surface of some cells; especially the major receptor of CD44. The regulatory effect of CD44 is widely accepted as a mark of the activated lymphocyte (referring to Teder P, Vandivier R W, Jiang D, Liang J, Crohn L, Pure E, Henson P M, Noble P W. Resolution of lung inflammation by CD44. Science 2002; 296: 155-158, Sheehan K M, DeLott L B, Day S M, DeHeer D H, Hyalgan has a dose-dependent differential effect on macrophage proliferation and cell death. J Orthop Res 2003; 21: 744-51).

The hyaluronic acid has the ability of creating and filling due to the organization and modification of the extracellular matrix, and is widely applied in filling the soft tissue for restraining the skin aging caused by age and light, as well as to adjust the obstacle of lipid metabolism on face, to prevent the increasing of secondary scar or scar formation on the skin.

Furthermore, the hyaluronic acid can be applied as the adjuvant agent for the eye operation or to reduce the pain while moving the knee and joint of the osteoarthritis patients.

Recently, the hyaluronic acid is applied in clinical treatment in the sodium salt form majorly in eye, skin, surgeon, artery treatment and in cosmetic fields. The hyaluronic acid with alkali metal ion, alkaline earth metal ion (for example the magnesium ion), aluminum ion, ammonium ion, and salt form of the replacement of the ammonium ion can be the carrier for assisting drug absorption (referring to Belgium Patent 904,547). The silver salt is used as the mycocide and the gold salt is used for treating the rheumatoid arthritis among the heavy metal salt of the hyaluronic acid (referring to WO 87/05517 of World Intellectual Property Organization).

The effect of treating the hipsore and the decubitus by the composition (complex) of the hyaluronic acid and the metal ion in the fourth group of periodic table, for example the zinc hyaluronate and the cobalt salt have been proven in the Hungary Patent 203,372 to the world.

Bioniche, the Canadian company, disclosed a method and related structure for using the hyaluronic acid with an effective concentration to treat cystitis in U.S. Pat. No. 5,888,986, wherein the Mw of the hyaluronic acid is more than 200,000 Da. There is only the hyaluronic acid with the certain Mw been applied in the embodiment thereof, for example, to use the hyaluronic acid with the 650 kDa or 1,900 kDa Mw to treat the cystitis; however, the single molecular weight of the hyaluronic acid can not be used for both prompt treatment and sustained effect.

The U.S. patent application Ser. No. 2005/0080037 (A1) belonging to Robert Peter Petrella, a Canadian, disclosed the use of hyaluronic acid for treating acute and over sprain and the reaction thereof, wherein the Mw of the hyaluronic acid is only between 90 thousand Da to 120 Da, and a single molecular weight of the hyaluronic acid cannot perform both prompt healing and prolonged action.

Seikagaku Kogyo, a Japanese company, has filed a U.S. Pat. No. 7,354,910 on Apr. 4, 2008 entitled "Use of Agent for treating inflammatory bowel disease" to disclose that the hyaluronic acid and hyaluronate with Mw between 600 kDa and 1,200 kDa can be applied to treat IBD. However, the degradation is too fast to retain the treating effect after injecting into the patient, therefore, it's very inconvenient for patients clinically.

SUMMARY OF THE INVENTION

An object of the present invention is to use the biological activity of at least two or more than two average molecular weight of hyaluronic acids in the pharmaceutically acceptable salt with different Mw to treat IBD (inflammatory bowel disease). Because the low average molecular weight hyaluronic acid (LMWHA) and the high average molecular weight hyaluronic acid (HMWHA) have different adhesive, insulated and degradation rate, the hyaluronic acid with average Mw lower than 1.5 million Da is categorized as LMWHA, and between 1.5 million and 5 million Da is categorized as HMWHA. Thus, mixture of LMWHA and HMWHA can form a desired formulation, wherein the LMWHA can rapidly cover the inflammatory surface to treat IBD (for example, ulcerative colitis, acute enteritis, chronic enteritis, Crohn's disease or the wound healing in the stomach and intestine), and the HMWHA can prolong the degradation in order to achieve a longer effective period. Thus, a faster treatment and a sustained release effect may be achieved.

The molecular weight of the hyaluronic acid applied in the present invention is preferably between 1.5 million and 3.5 million Da of the high average molecular weight hyaluronic acid (HMWHA), and more preferably between 2 million Da of high average molecular weight hyaluronic acid (HMWHA). The Mw of the hyaluronic acid applied in the present invention is more preferably between 0.5 million and 1.5 million Da of the low average molecular weight hyaluronic acid (LMWHA), and more preferably 1 million Da of low average molecular weight hyaluronic acid (LMWHA).

Another object of the present invention is to provide a hyaluronic acid mixture comprising both LMWHA and HMWHA together with a steroid, immunosuppressive agent or anti-inflammatory drug in order to potentiate the effect.

Another object of the present invention is to provide a hyaluronic acid mixture comprising both LMWHA and HMWHA forming the major active ingredient with the proper excipient (for example but not limited to gelatin, collagen, chitosan, chondroitin, carbopol, agar, carboxymethyl cellulose (CMC) or phosphate buffered saline (PBS), at least one of the foresaid item or the compound of the foresaid items) preparation to formulate as tablet (ex: enteric coated tablet), suppository (rectum suppository), perfusate fluid (for rectum or colon). The foresaid pharmaceutical preparation is accomplished by the common art in the field.

Another object of the present invention is to provide a concentration of a hyaluronic acid mixture comprising both LMWHA and HMWHA or the pharmaceutically acceptable salt thereof in a range from 0.5 mg/ml to 50 mg/ml, and preferable concentration is between 0.5 mg/ml to 5 mg/ml; a concentration in the solution form is in a range from 0.05% to 5% (w/v) and the preferable concentration is between 0.05% (w/v) to 0.5% (w/v).

The preferred dosage of the oral treat or prevention drug in the present invention is at least 10 to 1000 mg per administration, and the more preferred dosage is 10 to 500 mg per administration.

BRIEF DESCRIPTION OF THE DRAWINGS

FIG. 1 illustrates a recovery of the colonial lesion in mice of the treating group comparing with control group.

DETAIL DESCRIPTION OF THE INVENTION

The hyaluronic acid mixture of the present invention used to treat and to prevent the IBD comprises using at least two or more than two average molecular weight of hyaluronic acids including mixture of low average molecular weight hyaluronic acid (LMWHA) and high average molecular weight hyaluronic acid (HMWHA). The HMWHA and the LMWHA can be formed in a linear HA, a cross linked HA or a combination of at least one of the foresaid item. Different Mw has different rheology, functions of tissue scaffold and insulated and degradation in the solution, and therefore, the hyaluronic acid mixture has better adhesives and insulation and the tissue scaffold functions to balance the therapeutic effect and the degradation rate in order to treat and to prevent IBD (for example, ulcerative colitis, acute colitis, chronic colitis, Crohn's disease or to heal the wounds of the stomach and the intestines), as well as to achieve a proper treatment effect and a prolonged treatment effect.

The average Mw lower than 1.5 million Da is categorized as LMWHA, and preferable within a range between 0.5 million to 1.5 million Da. The average Mw higher than 1.5 million Da is categorized as HMWHA, and the Mw is within a range between 1.5 million to 5 million Da. The formulation containing a mixture of LMWHA and HMWHA, wherein the LMWHA promptly covers the inflammatory portion to treat and to prevent IBD, and the HMWHA extends the treatment effect. Thus, achieve prompt treatment and sustained release effect.

The Mw of the hyaluronic acid applied in the present invention is preferably between 1.5 million and 3.5 million Da of the high average molecular weight hyaluronic acid (HMWHA), and the more preferable between 2 million Da of high average molecular weight hyaluronic acid (HMWHA). The Mw of the hyaluronic acid applied in the present invention is more preferably between 0.5 million and 1.5 million Da of the low average molecular weight hyaluronic acid (LMWHA), and is more preferably between 1 million Da of low average molecular weight hyaluronic acid (LMWHA).

The general chemical structure of the hyaluronan may be illustrated as follows.

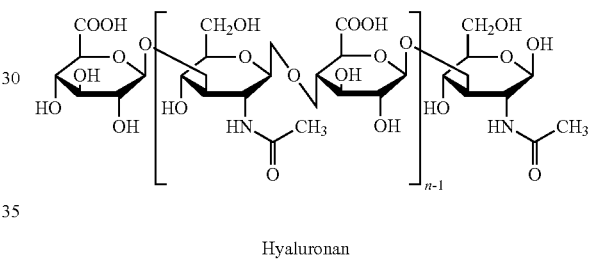

Hyaluronan

Another preferred embodiment of the present invention includes a 1:1 mixture of LMWHA and HMWHA of the hyaluronic acid, and the ratio or the salt form may be adjusted depending on the clinical purpose between 20:80 and 80:20. The hyaluronic acid mixture with a higher ratio of LMWHA can be more helpful in speeding up the treatment; on the contrary, a higher ratio of HMWHA can provide a better degradation rate to prolong the treatment effect.

Another preferred embodiment of the present invention includes a hyaluronic acid mixture including LMWHA and HMWHA together with a steroid, immunosuppressive agent or other anti-inflammatory drug to potentiate the effect.

Another preferred embodiment of the present invention includes a hyaluronic acid mixture including both LMWHA and HMWHA constituting the major active ingredient with the proper excipient to formulate an oral solid dosage form (for example enteric coating), suppository (rectal suppository), perfusate fluid (for the rectum or the colon).

For oral formulation (for example enteric coated tablet), the enteric coating provides more resistance dissolution and digestion in the stomach, and after reaching intestine and colon, the enteric coating will be dissolved and the hyaluronic acid will be released to form a protection membrane at the inflammatory colon (the region uprising ascending colon or Transverse colon) in order to accelerate healing of the inflammatory region and also to prolong the treatment effect by long degradation rate.

For suppository formulation, the suppository containing above hyaluronic acid may be inserted into the anus and the hyaluronic acid will be released in the rectum and spread to other region of colon (for example the descending region) to form a protection membrane at the inflammatory colon in order to accelerate healing of the inflammatory region and also achieve sustained release effect.

For perfusion formulation (for example enema), the above hyaluronic acid mixture is the major active ingredient mixed with the excipient (for example but not limited to gelatin, collagen, chitosan, chondroitin, carbopol, agar, carboxymethyl cellulose (CMC) or phosphate buffered saline (PBS), at least one of the foresaid item or the compound of the foresaid items) directly used or in a soft tube to inject the above hyaluronic acid mixture into the colon. The hyaluronic acid mixture will be charged into the colon and spread to other region of colon (for example the descending region) to form a protection membrane at the inflammatory colon in order to accelerate the healing of the inflamed region and also achieve sustained release effect.

The preferred concentration of the hyaluronic acid mixture including LMWHA and HMWHA or pharmaceutically acceptable salt thereof ranges from 0.5 mg/ml to 5 mg/ml, but the preferred concentration in the solution form is within a range from 0.05% to 0.5% (w/v). The concentration is between 0.5 mg/ml to 50 mg/ml, and the preferred concentration is between 0.5 mg/ml to 5 mg/ml. The solution may be preferably formed in the concentration ranged from 0.05 to 5% (w/v); the more preferred solution formed in the concentration ranged from 0.05 to 0.5% (w/v). Furthermore, as for oral administration for prevention or improvement the preferred dose is at least 10 to 500 mg for each administration, and the pharmaceutically acceptable salt of the hyaluronic acid mixture is the sodium hyaluronan and the zinc hyaluronan.

Furthermore, the LMWHA in the Mw and the HMWHA in the Mw of the present invention can be applied accompanied with the steroid, immunosuppressive agent or anti inflammatory drug in order to achieve the better treatment effect.

For presenting the proof of the effect of the hyaluronic acid mixture in the present invention, the animal test performed under the professional laboratory is resulted as the following report:

Embodiment 1 (Referring to the Attachment)

1-1 Abstract: The propose of the test is to evaluate the effect of the sample IBD98 in the animal body having the IBD. IBD98 was inserted into the rectum of the mice of the preventive group, then trinitrobenzenesulphonic acid (TNBS) was administered to induce the enteritis disease; followed up with continuous administration of the sample IBD98 through rectum for 3 days. Only administered the TNBS to the control group to induce the IBD. After 3 days of observation, all the mice were sacrificed on the $4^{th}$ day to inspect the clinical pathological changes, the index of blood sample before administrating the drug and after the termination of the test. The result indicates averages of the colonial inflammatory range of the preventive and control groups were 3.9 cm and 4.3 cm, which indicated no significant difference. The mice of the preventive and control groups have significant difference in the concentration of the TNF-α (Tumor Necrosis Factor-alfa) and IL-1β (Interleukin-1β), indicating that the mice had the substantial induced inflammatory; the concentration of TNF-α of the preventive group after determination the test is significantly lower than the control group, and the difference is obvious. However, there was no significant difference in the concentration of IL-1β. The test has confirmed that such pattern can induce IBD in animal body and there is no significant difference in the clinical pathological change. Therefore, the effect on the sample can be evaluated by observing the recovering status after administrating the IBD98 sample. The test result indicates there is significant difference in the TNF-α in the preventive and control group performance. Therefore, the result proves that the IBD98 sample is substantially effective in reducing the inflammatory reaction in order to prevent the IBD.

1-2 Test Procedure:

A. Test Propose: to induce the IBD to the mice with the TNBS in order to evaluate the effect for treating or prevention of IBD or to reduce the inflammatory.

B. Test Objective:
  IBD98, comprising LMWHA and HMWHA, and the HMWHA in a 2 million Da range and the LMWHA in a 1 million Da range, mixed in the ratio of 1:1, dissolved in PBS solution to produce a concentration of 0.5%.

C. Method:
  1. Test Target:
     Selected 30 8-week old SPF grade Sprague Dawley male mice, and classified into two groups, each group containing 15 mice, and keep two mice in one cage set in the observation room of the laboratory.
  2. Animal Test:
     The mice were fasted for over 24 hours in the preventive group; test day 1, anesthetized the mice for administrating 1 ml of IBD98 via the rectum, and then administered 1 ml of TNBS (50 mg/mL) via the rectum; test day 2 to 4, administered 1 ml of IBD98 via the rectum; test day 5, sacrificed all mice to observe the colon for observing the clinical pathological changes.

Fasted the mice for over 24 hours in the control group; test day 1, and then anesthetized the mice for administrating 1 ml of TNBS (50 mg/mL) via the rectum; test day 2 to 4, administered 1 ml of PBS via the rectum; test day 5, and then sacrificed all mice to observe the colon for observing the clinical pathological changes.

3. Inflammatory Index Text
     Took the blood sample from the vein of the tail of the mice in both preventive and control groups on day 1 before starting the test, and then took blood sample from the heart after determination of the test; and collected the serum after centrifugation and inspected the serum for the changes of the TNF-α and IL-1β by ELISA (enzyme-linked immunosuppressant assay) respectively.

1-3 Test Figures:

CHART 1 clinical colonial pathological changes of the mice on the preventive group and control group

| preventive group | | | control group | | |
| --- | --- | --- | --- | --- | --- |
| obj. no. | inflam. Range (cm) | ulcer lesion grade | obj. no | inflam. Range (cm) | ulcer lesion grade |
| A-2 | 2.5 | 1 | 2 | B1 | 2.5 | 0 | 2 |
| A-3 | 5 | 2 | 4 | B2 | 3.5 | 0 | 2 |
| A-4 | 4.5 | 1 | 3 | B3 | 4 | 1 | 3 |
| A-5 | 3.5 | 0 | 2 | B4 | 6 | 2 | 4 |
| A-6 | 4 | 1 | 3 | B5 | 5 | 2 | 4 |
| A-7 | 5.5 | 2 | 4 | B7 | 6 | 3 | 4 |
| A-8 | 4 | 1 | 3 | B8 | 4 | 1 | 3 |
| A-9 | 2.5 | 0 | 2 | B9 | 6 | 2 | 4 |
| A-10 | 4 | 1 | 3 | B11 | 1.5 | 0 | 1 |
| A-11 | 2 | 0 | 2 | B13 | 1.5 | 0 | 1 |
| A-13 | 6.5 | 2 | 4 | B14 | 6.5 | 3 | 4 |
| A-14 | 3 | 1 | 2 | B15 | 5 | 2 | 4 |

CHART 1-continued clinical colonial pathological changes of the
mice on the preventive group and control group

| preventive group | | | control group | | |
|---|---|---|---|---|---|
| obj. no. | inflam. Range (cm) | ulcer lesion grade | obj. no | inflam. Range (cm) | ulcer lesion grade |
| A-15 | 4 | 1 | 3 | | |
| average | 3.9 | 1 | | 4.3 | 1.3 |

CHART 2 changes of the TNF-α and IL-1β in the serum of the mice before (D1)
and 4 days after (D5) administration the drug to both the preventive

| | Preventive group | | | | | Control group | | | |
|---|---|---|---|---|---|---|---|---|---|
| Obj. | TNF-α (pg/mL) | | IL-β (pg/mL) | | Obj. | TNF-α (pg/mL) | | IL-β (pg/mL) | |
| no. | D1 | D5 | D1 | D1 | no. | D1 | D5 | D1 | D5 |
| A2 | 27.8 | 1933.7 | 0 | 869.6 | B1 | 14.3 | 586.5 | 1.0 | 42.1 |
| A3 | 28.6 | 847.8 | 29.6 | 94.8 | B2 | 23.1 | 2241.5 | 21.8 | 1325.2 |
| A4 | 22.2 | 110.3 | 0.7 | 44.8 | B3 | 26.6 | 1608.5 | 20.4 | 1680.1 |
| A5 | 12.8 | 481.9 | 0 | 130.3 | B4 | 22.2 | 1933.7 | 54.1 | 1229.8 |
| A6 | 25.6 | 1347.2 | 6.9 | 790.3 | B5 | 7.9 | 847.8 | 0 | 21.9 |
| A7 | 9.6 | 36.6 | 0 | 16.9 | B7 | 6.4 | 1068.5 | 0 | 29.4 |
| A8 | 18.7 | 458.7 | 0 | 39.1 | B8 | 15.4 | 2090.5 | 17.8 | 962.3 |
| A9 | 17.5 | 528.4 | 0 | 33.9 | B9 | 17.9 | 1498.2 | 0 | 46.9 |
| A10 | 16.3 | 1736.3 | 0 | 401.8 | B11 | 0.7 | 1387.9 | 22.3 | 197.5 |
| A11 | 10.3 | 331.0 | 0 | 11.3 | B13 | 1.0 | 714.2 | 23.4 | 25.0 |
| A13 | 30.1 | 1440.1 | 0 | 1069.8 | B14 | 0 | 1649.2 | 1.3 | 32.7 |
| A14 | 18.0 | 540.0 | 0 | 47.3 | B15 | 12.4 | 569.1 | 6.5 | 39.8 |
| A15 | 38.9 | 79.1 | 5.6 | 35.4 | | | | | |
| Ave. | 21.3 | 759.3** | 3.3 | 275.8* | Ave. | 12.3 | 1349.6**# | 14.1 | 469.4* |

**the concentration of the TNF-α in the serum of the preventive group mice in D5 and D1 has significant difference ($P < 0.01$), as well as the control group ($P < 0.01$).
*the concentration of the IL-β in the serum of the preventive group mice in D5 and D1 has significant difference ($P < 0.05$), as well as the control group ($P < 0.05$).
the concentration of the TNF-α in the serum of the preventive group and control mice in D5 and D1 has significant difference ($P < 0.05$).

1-4 Test Result 30 mice were selected for performing the test and separate them into two groups as the preventive group and the control group, each group contains 15 mice and then fasted over 24 hours before running the test, and administering the enema for exhausting the faeces before administrating drug. Administered 1 mL of TNBS to the control group on Day 1 (D1) and administered PBS for the following 3 days (D2-D4); administered 1 mL of TNBS to the preventive group on Day 1 (D1), and then administered 1 mL of IBD98 after an hour, and then continued to administered IBD98 for the following 3 days (D2-D4). The mice of both groups on Day 5 (D5) were sacrificed for further performing dissection to inspect the intestinal lesion and the inflammatory range. The mice dead during the test process are not accounted for the result of the test. There were 13 mice accountable in the preventive group and 12 in the control group at the end of the test. The average of the inflammatory range of the preventive group and the control group are respectively as 3.9 cm and 4.3 cm, which have insignificant difference (referring to chart 1).

The average concentration (pg/mL) of the inflammatory index TNF-α on D1 and D5 was observed to have risen from 21.3 to 759.3 in the preventive group and from 12.3 to 1349.6 in the control group, which indicates the significant difference ($P<0.01$); the average concentration (pg/mL) of the inflammatory index IL-1β on D1 and D5 was observed to have risen from 3.3 to 275.8 in the preventive group and from 14.1 to 469.4 in the control group, which indicates the significant difference ($P<0.05$) as well. The indication shows that before inducing TNBS, the mice of the test substantially appeared the inflammatory reaction. Comparing the inflammatory index of the two groups after the continuous process of 3 days on Day 5, the average concentration of TNF-α is 759.3 in the preventive group, 1349.6 in the control group, there was a significant difference between these two groups ($P<0.05$); and the concentration of the TNF-α in the serum of the preventive group is substantially significantly lower than the control group. In other words, the mice treated with IBD98 had less inflammation than the untreated mice (referring to chart 2).

1-5 Conclusion

The IBD was induced in the both groups, in the following 3 days, the control group received no medical treatment and the preventive group was treated with the TNBS after treated with IBD98, the concentration of both TNF-α and IL-1β of the inflammatory index in the two groups are substantially risen, which indicates the inflammatory relation was induced in the mice. The TNF-a concentration of the preventive group was significantly lower than the control group, which means there is a substantial effect for reducing the inflammatory reaction to the mice after treated with the IBD98.

Embodiment 2 (referring to attachment)

2-1 Abstract

IBD was induced in the tested animals is to evaluate the effect of the IBD98 among the animal body. TNBS was administered to the mice in the rectum to induce the intestinal lesion, and then the IBD98 sample was administered into the mice of the treating group and PBS (phosphate buffered saline) to the control group respectively via the rectum after 3 days. The mice were sacrificed after 7 days of the continuous treatment to inspect the clinical lesion. The result indicates the colonial inflammatory range is averagely about 1.25 cm in the treating group treated with the IBD98 sample, and 1.875 cm in the control group treated with PBS. There is 33% of the recovery comparing the treating group with the control group. In other words, the IBD in the mice treated with IBD98 is substantially advantageous for the recovery of the intestine tissue.

2-2 Test Process
A. Test Purpose:
To induce the IBD in the mice by administrating the TNBS and to evaluate whether IBD98 is advantageous for treating or preventing the IBD or reducing the inflammatory in the mice.
B. Test Object
IBD98, comprising LMWHA and HMWHA, and the HMWHA in a 2 million Da range and the LMWHA in a 1 million Da range, mixed in the ratio of 7:3, dissolved in PBS solution to obtain a concentration of 0.5%.
D. Method:
4. Test Target
36 8-week old SPF grade Sprague Dawley male mice were selected and classified into two groups, each group containing 18 mice, and keeping two mice in one cage set in the observation room of the laboratory.
5. Animal Test
The mice were fasted for over 24 hours; test day 1, and then anesthetized for administrating 1 mL of TNBS (tri-nitro-benzene sulphonic acid, 50 mg/mL) via the rectum, and then observed for 3 days, and picked out the mice with the soft stool or the diarrhea symptom on the third day.
The mice of the treating group were anesthetized for administrating 1 mL of the IBD98 (5 mg/mL) on Day 4 to Day 10. The mice of the control group were anesthetized for administrating 1 mL of the PBS on Day 4 to Day 10, and then all the mice were sacrificed on Day 11 to observe the colon for observing the clinical lesion.

2-3 Test Figures:

CHART 1 the clinical intestinal lesion in the mice of the control group

| Obj. no | Inflam. Range (cm) | Ulcer lesion | Clinical grade |
|---|---|---|---|
| B-12 | 2.0 | 1 | 2 |
| B-13 | 2.5 | 0 | 2 |
| A-18 | 1.0 | 0 | 1 |
| B-18 | 0 | 0 | 0 |
| B-14 | 0.3 | 0 | 1 |
| B-15 | 2.0 | 0 | 1 |
| Average | 1.875 | 0.17 | — |

CHART 2 the clinical lesion and the corresponding recovery ratio of the mice in the treating group

| Obj. no | Inflame. range (cm) | Ulcer lesion | Clinical grade | Corresponding recovery ratio* |
|---|---|---|---|---|
| A-11 | 2.0 | 0 | 2 | 6.7 |
| A-15 | 1.5 | 0 | 1 | −20.0 |
| A-17 | 2.0 | 0 | 2 | 6.7 |
| A-3 | 1.5 | 0 | 1 | −20.0 |
| A-4 | 0.5 | 0 | 1 | −73.3 |
| B-6 | 0.5 | 0 | 1 | −73.3 |
| A-13 | 2.0 | 0 | 1 | 6.7 |
| A-16 | 0.3 | 0 | 1 | −84.0 |
| B-4 | 1.0 | 0 | 1 | −46.7 |
| Average | 1.25 | 0 | — | −33.0 |

*Corresponding recovery ratio (%) = inflammatory range in the treating group − average of the inflammatory range in the control group/average of the inflammatory range in the treating group 2-4 Test Result:
36 mice were selected for performing the test and separated them into the treating group and the control group with 18 mice in each group. The mice were fasted for over 24 hours before the test. Enema was administered to exhaust the faeces and administer the TNBS before administrating drug. After observing for 3 days, two mice died and 5 confirmed with the IBD by the dissection. The mice with normal stool status were excluded, the mice with soft stool and diarrhea on Day 4 were considered. IBD98 was continued to be administered via the rectum of the 10 mice in the treating group and administered PBS to 7 mice in the control group for 7 days (D4 to D10). Each group lost one mouse during the test, and then all mice were sacrificed on Day 11 for inspecting the intestinal lesion and the inflammatory range.

In the control group, one mouse had no lesion, three mice had local inflammatory for 0.3 to 1 cm and grade 1 lesion, and two mice had local inflammatory for 2 to 2.5 cm and grade 2 lesion (referring to chart 1). In the treating group, 7 mice had local inflammatory for 0.3 to 1.5 cm and grade 1 lesion, and two mice had local inflammatory for 2 cm and grade 2 lesion (referring to chart 2). After statistical analysis, the average inflammatory range in the mice of the control group is 1.875 cm and 1.25 cm in the mice of the treating group; the recovery ration is 33% compare the two groups (referring chart 2 and FIG. 1).

In conclusion, the present invention majorly applied the hyaluronic acid mixture comprising at least two or more than two pharmaceutically acceptable hyaluronic acid in the salt form with various Mw (molecular weight), and the various degradation rates among various Mw enables the LMWHA with low Mw to spread rapidly to the HMWHA with higher Mw to accordingly maintain the degradation for better subtend release effect, thus to achieve the goal of prompt treatment and retarding effect.

While the invention has been described in conjunction with a specific best mode, it is to be understood that many alternatives, modifications, and variations will be apparent to those skilled in the art in light of the foregoing description. Accordingly, it is intended to embrace all such alternatives, modifications, and variations in which fall within the spirit and scope of the included claims. All matters set forth herein or shown in the accompanying drawings are to be interpreted in an illustrative and non-limiting sense.

What the invention claimed is:

1. A mixture of hyaluronic acid for treating inflammatory bowel disease (IBD) consisting essentially of hyaluronic acids with a lower molecule weight (Mw of LMWHA) and a higher molecule weight (Mw of HMWHA); an average Mw of LMWHA is 1 million Da, and an average Mw of HMWHA is 2 million Da; and a mixing ratio of said LMWHA and said HMWHA is in a range from 20:80 to 80:20,
wherein the concentration of the mixture of said LMWHA and said HMWHA in a solution is 0.5 mg/mL to 50 mg/mL.

2. The mixture of hyaluronic acid for treating inflammatory bowel disease (IBD) according to claim 1, wherein said mixing ratio of said LMWHA and said HMWHA is 1:1.

3. The mixture of the hyaluronic acid for treating inflammatory bowel disease (IBD) according to claim 1, wherein the concentration of the mixture of said LMWHA and said HMWHA in a solution is 0.5 mg/mL to 5 mg/mL.

4. The mixture of hyaluronic acid for treating inflammatory bowel disease (IBD) according to claim 1, wherein said hyaluronic acid mixture includes an excipient to formulate an oral solid dosage form.

5. The mixture of hyaluronic acid for treating inflammatory bowel disease (IBD) according to claim 1, wherein said hyaluronic acid mixture includes an excipient to formulate suppositories, or a rectal or perfusate.

6. The mixture of hyaluronic acid for treating inflammatory bowel disease (IBD) according to claim 1, wherein said hyaluronic acid mixture is further combined with a steroid, immunosuppressive agent or anti-inflammatory drug.

7. The mixture of hyaluronic acid for treating inflammatory bowel disease (IBD) according to claim 1, wherein said hyaluronic acid mixture is used to treat and prevent ulcerative colitis, acute enteritis, chronic enteritis or Crohn's disease and to aid in healing stomach and intestine wounds.

8. A mixture of hyaluronic acid consisting essentially of hyaluronic acids with a lower molecule weight (Mw of LMWHA) and a higher molecule weight (Mw of HMWHA); an average Mw of LMWHA is 1 million Da, and an average Mw of HMWHA is 2 million Da; and a mixing ratio of said LMWHA and said HMWHA is in a range from 20:80 to 80:20;
    wherein the concentration of the mixture of said LMWHA and said HMWHA in a solution is 0.5 mg/mL to 50 mg/mL; and
    wherein said mixture of hyaluronic acid is used for treating inflammatory bowel disease (IBD) or irritable bowel syndrome (IBS).

\* \* \* \* \*